United States Patent [19]

Jensen et al.

[11] Patent Number: 4,552,146
[45] Date of Patent: Nov. 12, 1985

[54] DISPOSABLE OPHTHALMIC INSTRUMENT FOR PERFORMING RADIAL KERATOTOMY ON THE CORNEA

[75] Inventors: Ronald P. Jensen; Arthur N. Allcroft, both of Glendale, Calif.

[73] Assignee: Myocur, Inc., Los Angeles, Calif.

[21] Appl. No.: 567,263

[22] Filed: Dec. 30, 1983

Related U.S. Application Data

[63] Continuation-in-part of Ser. No. 379,362, May 18, 1982, abandoned.

[51] Int. Cl.⁴ .................... A61B 17/32; B26B 29/00
[52] U.S. Cl. ................................. 128/305; 30/293
[58] Field of Search .............. 128/305, 305.1, 314; 30/286, 289, 290, 293, 294

[56] References Cited

U.S. PATENT DOCUMENTS

| | | | |
|---|---|---|---|
| 3,776,230 | 12/1973 | Neefe | 604/291 |
| 3,789,830 | 2/1975 | Malmstrom | 128/314 |
| 3,945,117 | 3/1976 | Beaver | 128/305 X |
| 4,006,746 | 2/1977 | Edwards | 128/305 |
| 4,026,295 | 5/1977 | Lieberman | 128/305 |
| 4,180,075 | 12/1979 | Marinoff | 128/305 |
| 4,205,682 | 6/1980 | Crock et al. | 128/305 |
| 4,298,004 | 11/1981 | Schachar | 128/305 |
| 4,340,059 | 7/1982 | Marinoff | 128/305 |

Primary Examiner—Stephen C. Pellergino
Attorney, Agent, or Firm—Christie, Parker & Hale

[57] ABSTRACT

The present invention is an ophthalmic instrument for use in performing radial keratotomy on the cornea of a patient for correcting myopia and/or astigmatism of the patient. The ophthalmic instrument includes a surgical blade having a suitable width for making an incision into the cornea of the patient and an elongated handle which is formed out of a plastic material and to which the surgical blade is fixedly coupled. The ophthalmic instrument also includes a depth-guide which is a hollow, cylindrical member and which is formed out of a plastic material. The depth guide has a first and second end and also has a pair of protruding arms, each of which has a first end and a rounded second end and which extend parallel to each other and to the longitudinal axis of the hollow, cylindrical member from the first ends of the protruding arms for most of their length and then sharply converge adjacent, but not contiguous to the rounded second ends of the protruding arms the second ends of the protruding arms being spaced apart a distance slightly greater than the width of the surgical blade whereby the second rounded ends of the protruding arm slidably rests on the surface of the cornea in order to control the incision depth of the surgical blade, slidably coupled to the elongated handle. The depth-guide has it position on the elongated handle pre-set to a depth in the range of 0.20 millimeters to 1.2 millimeters.

3 Claims, 9 Drawing Figures

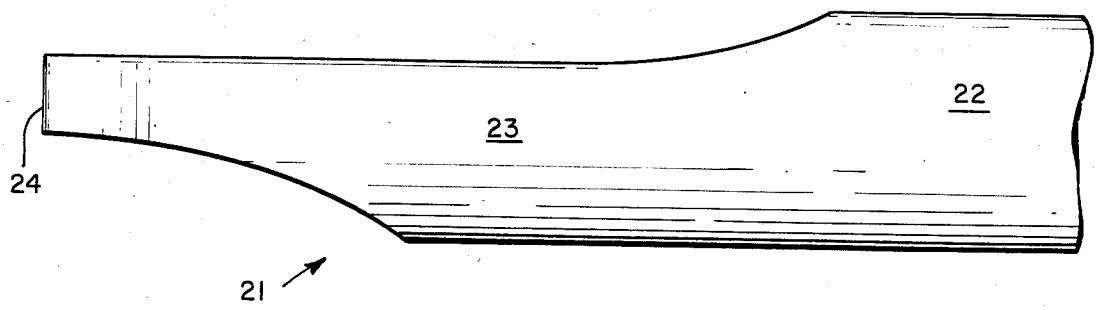
Fig. 6.
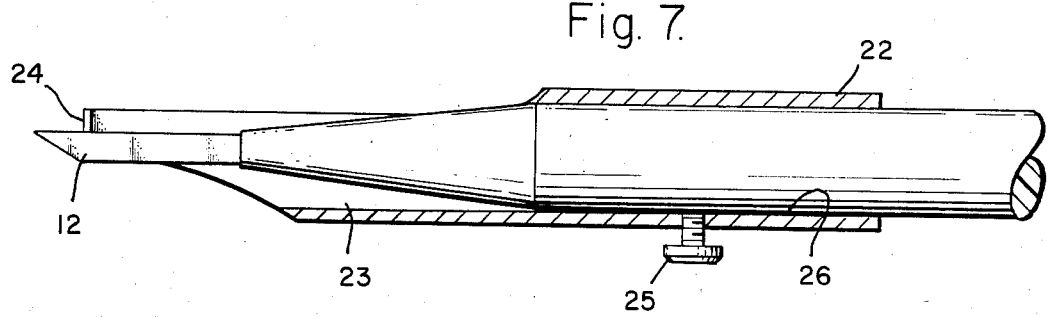
Fig. 7.
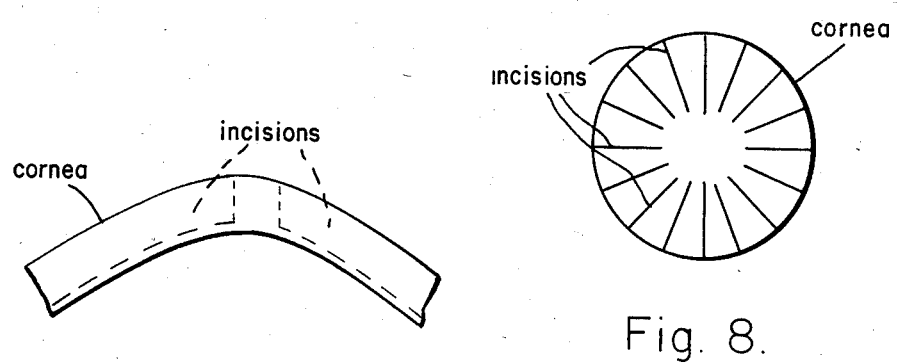
Fig. 8.
Fig. 9.
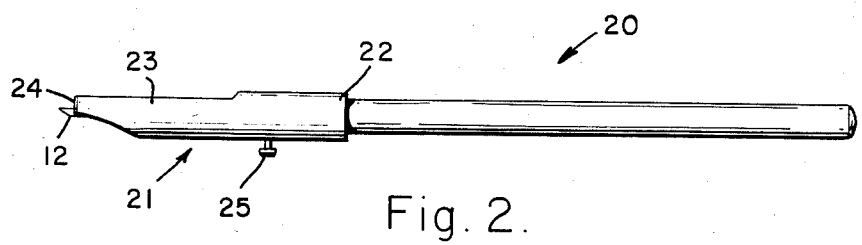
Fig. 2.

4,552,146

DISPOSABLE OPHTHALMIC INSTRUMENT FOR PERFORMING RADIAL KERATOTOMY ON THE CORNEA

CROSS-REFERENCE TO RELATED APPLICATION

This is a continuation-in-part of application Ser. No. 379,362 filed May 18, 1982, now abandoned.

FIELD OF THE INVENTION

The present invention relates to an ophthalmic instrument for performing the procedure of radial keratotomy on a cornea and more particularly to a disposable ophthalmic surgical knife having a guide foot which has been pre-set at a particuliar depth and which does not block the view of the ophthalmologist while he is making the incisions in the cornea.

BACKGROUND OF THE INVENTION

U.S. Pat. No. 3,776,230, entitled Method of Rapidly Reshaping the Cornea to Eliminate Refractice Errors, issued to Charles W. Neefe on Dec. 3, 1973, teaches a method of correcting the refractive errors of the eye by changing the shape of the cornea by softening the cornea tissue by the application of heat and reshaping the convex cornea to the curvature of the surface of a concave mold which is applied to the cornea.

U.S. Pat. No. 4,298,004, entitled Surgical Method for altering the Curvature of the Cornea of Rabbits, issued to Ronald A. Schachar and Norman S. Levy on Nov. 3, 1981, teaches a method for altering the radius of curvature of the cornea together with an appratus for use therein. The apparatus includes a circular ring which can be placed over the eye for concentrically surrounding the cornea and blade which is mounted for retractable movement to and away from the cornea. The blade is also able to rotate through a limited arc so that a sector shaped incision can be made in the cornea. Collagen is injected into the sector-shaped incision to alter the radius of curvature of the cornea.

U.S. Pat. No. 4,180,075, entitled Ophthalmological Surgical Instrument, issued to Gerald P. Marinoff on Dec. 25, 1979, teaches a hand held surgical instrument for performing ophthalmological incision in the form of an arc for cataract surgery.

Ophthalmologists have long been concerned with correcting the hyperopia in the eye and defects which relate to the curvature of the cornea. A well-known method for correcting hyperopia includes corrective lenses, such as eye glasses or contact lenses. These methods have obvious drawbacks as they do not form an integral part of the eye structure. Eye glasses and contact lenses are often bothersome to wear and are subject to loss or breakage. Contact lenses present additional problems such as eye infections and corneal damage related to excessive abrasion and scratching.

A need therefore existed for a method and apparatus for correcting hyperopia without external corrective lenses. Further, a need also existed for the correction of hyperopia wherein the radius of curvature of the cornea is permanently altered.

Svyatoslav N. Fyodorov, M.D., and Valery V. Durnev, in an article entitled "Operation of Dosaged Dissection of Corneal Circular Ligament in Cases of Myopia of Mild Degree", published in the *Annals of Ophthalmology*, December, 1979, pages 1885–1890, reported their results of using radial keratotomy on 60 eyes of 30 patients who had bilateral, non-progressive myopia ranging from 0.75 to 3.0 diopters. The central optical zone was delimited by a light touch of a marker. The cornea was then marked by lines forming 16 even segments by a special device with the markings resembling the spokes of a wheel and the delimited optical zone resembling the hub of the wheel. A razor blade in a blade holder was used to make 16 radial partial thickness incisions of the cornea along the lines forming the 16 even segments from the border of the delimited central optical zone to the limbus. The depth of the incision approaches three-fourths of the thickness of the cornea. Following the procedures, the eye was irrigated with a weak physiological saline solution. A solution of antibiotic was then injected under the conjunctiva and the eye patched.

In the article, Fyodorov and Durnev stated that a guarded blade had been used by Sato who published in 1953 an article entitled "A New Surgical Approach to Myopia", in the *American Journal of Ophthalmology*, Volume 36, page 823.

U.S. Pat. No. 3,945,117, entitled Surgical Blade with Adjustable Blade Guard, issued to John R. Beaver on May 23, 1976, teaches a surgical knife assembly in which a blade is provided with a guard for limiting the depth guard for limiting the depth of cut. The guard is formed of a resilient material as plastic, and frictionally grips the blade, so that the guard is adjustable on the blade by the application of a predetermined amount of axial force, with the force required for adjustment being considerably greater than the force that is applied thereto during a cutting procedure. An adjustment tool is also provided, the tool and the blade having cooperating engaging portions to permit accurate adjustment of the position of the guard on the blade between incisions during a surgical procedure.

U.S. Pat. No. 4,006,746, entitled Surgical Knife, issued to John Edwards on Feb. 8, 1977, teaches a manual surgical knife which includes an elongated knife blade and an elongated blade guide.

U.S. Pat. No. 4,026,295, entitled Surgical Knife, issued to David M. Lieberman on May 31, 1977, teaches a surgical knife for achieving a precise incision for cataract extraction.

U.S. Pat. No. 3,789,830, entitled Disposable Lancet, issued to Sven-Erik Malmstrom on Feb. 5, 1974, teaches multiple disposable lancets which are punched from a strip of sheet steel in order to obtain economy in the manufacturing operation.

SUMMARY OF THE INVENTION

In view of the foregoing factors and conditions which are characteristic of the prior art, an ophthalmic instrument is set forth for performing the procedure of radial keratotomy on the cornea of a patient which is a surgical knife having a guide foot which has been pre-set at a particular depth. The ophthalmic instrument is disposable and is adapted so as to not block the view of the ophthalmologist while he is making incisions in the cornea of a patient.

In accordance with the present invention, the embodiment of an ophthalmic instrument for use in performing radial keratotomy on the cornea of a patient for correcting myopia and/or astigmatism of the patient is described. The ophthalmic instrument includes a surgical blade having a suitable width for making an incision into the cornea of the patient and an elongated handle which is formed out of a plastic material and to which the surgical blade is fixedly coupled. The ophthalmic instrument also includes a depth-guide which is a hollow, cylindrical member and which is formed out of a plastic material. The depth guide has a first and second end and also has a pair of a protruding arms, each of which has a first end and a rounded second end and which extend parallel to each other and to the longitudinal axis of the hollow, cylindrical member from the first ends of the protruding arms for most of their length and then sharply converge adjacent, but not contiguous to the rounded second ends of the protruding arms, the second ends of the protruding arms being spaced apart a distance slightly greater than the width of the surgical blade whereby the second rounded ends of the protruding arm slidably rest on the surface of the cornea in order to control the incision depth of the surgical blade, slidably coupled to the elongated handle. The depth-guide has its position on the elongated handle pre-set to a depth in the range of 0.20 millimeters to 1.2 millimeters.

BRIEF DESCRIPTION OF THE DRAWINGS

FIG. 2 is a side elevational view of an ophthalmic instrument for performing radial keratotomy on the cornea of a patient which has been constructed in accordance with the principles of the present invention;

FIG. 6 is a side elevational view of the depth-guide of FIG. 3;

FIG. 7 is a side elevational view in cross-section of the depth-guide of FIG. 3;

FIG. 8 is a diagramatic drawing of the cornea showing the placement of the incisions which are made during the procedures of radial keratotomy; and FIG. 9 is a diagramatic drawing of a side elevational view of the cornea showing the depth of the incisions of FIG. 8.

DETAILED DESCRIPTION

Figure 1:
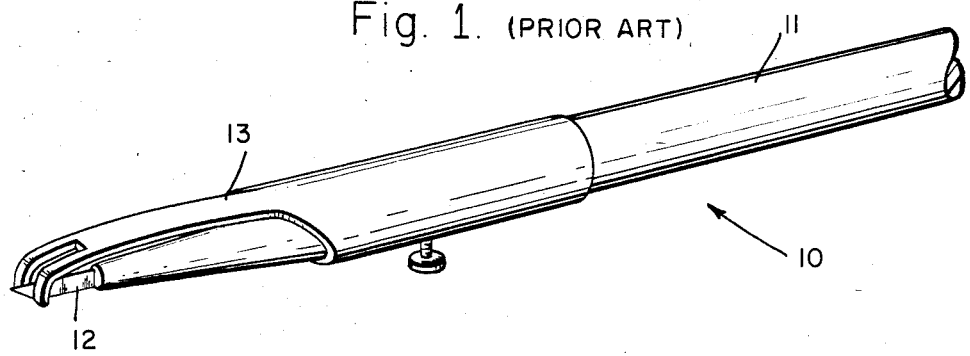
FIG. 1 is a perspective drawing of a prior art ophthalmic instrument for performing radial keratotomy on the cornea of a patient.
Figure 3:
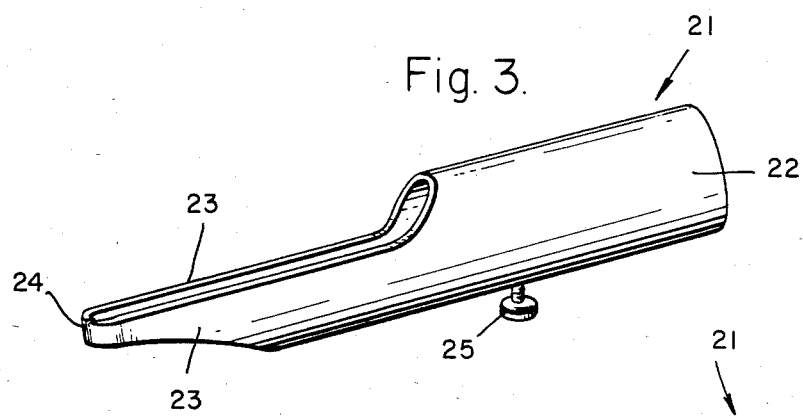
FIG. 3 is a perspective drawing of a depth-guide of the ophthalmic instrument of FIG. 2.
Figure 4:
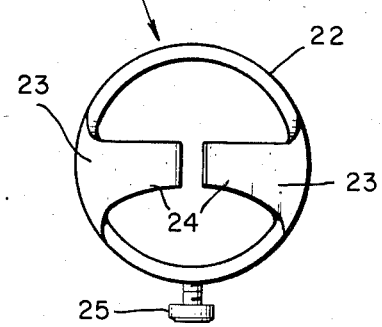
FIG. 4 is a front elevational view of the depth-guide of FIG. 3.
Figure 5:
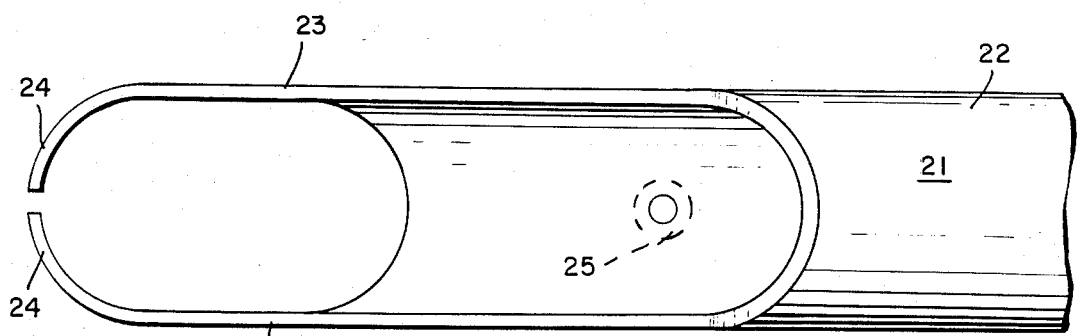
FIG. 5 is a top plan view of the depth-guide of FIG. 3.

In order to best understand the present invention, it is first necessary to refer to the following description of the prior art in conjunction with FIG. 1 of the drawing. Referring to FIG. 1, an ophthalmic instrument 10 includes an elongated handle 11 and a surgical blade 12 which is fixedly coupled to the elongated handle 11. The ophthalmic instrument 10 also includes depth-guide 13 which has a protruding arm which extends parallelly over the non-cutting edge of the surgical blade 12 and which has a pair of prongs extending further, but bending down so that the surgical blade 12 is disposed between them whereby the pair of prongs limit the incision depth of the ophthalmic instruction 10.

Referring to FIG. 2, an ophthalmic instrument 20 according to the present invention for use in performing radial keratotomy on the cornea of a patient for correcting myopia and/or astigmatism of the patient is set forth, the instrument 20 includes an elongated handle 11 and a surgical blade 12 being fixedly coupled to the elongated handle 11 and having a suitable width for making an incision into the cornea of the patient. The elongated handle 11 may be formed out of either a plastic material or a metallic material.

Referring to FIG. 2, in conjunction with FIGS. 3-7, the ophthalmic instrument 20 also includes a depth-guide 21 which is a hollow, cylindrical member 22 and which is formed out of either a plastic material or a metallic material. The depth guide 21 has a first and second end and also has a pair of a protruding arms 23, each of which has a first end and a rounded second end 24 and which extend parallel to each other and to the longitudinal axis of the hollow, cylindrical member 22 from the first ends of the protruding arms 23 for most of their length and then sharply converge adjacent, but not contiguous to the rounded second ends 24 of the protruding arms 23. The rounded second ends 24 of the protruding arms 23 are spaced apart a distance slightly greater than the width of the surgical blade 12 whereby the round second ends 24 of the protruding arm 23 slidably rest on the surface of the cornea in order to control the incision depth of the surgical blade 12. The depth-guide 21 is slidably coupled to the elongated handle 11. The depth-guide 21 has its position on the elongated handle 11 pre-set to a depth in the range of 0.20 millimeters to 1.2 millimeters. A set screw 25 or a solder tack secures the depth-guide in place.

In their article, Steven G. Kramer, Edward Q. Yavitz and Jukka Sulonen, entitled "Precision Standardization of Radial Keratotomy", published in *Ophthalmic Surgery*, August, 1981, Volume 12, Number 8, pages 561-566, discuss the need for a precision ophthalmic instrument for performing the procedure of radial keratotomy on the cornea of a patient. They recommend a suction template with a central opening for a visual axis. The key to the ophthalmic instrument 20 according to the present invention is that it is a surgical knife which has a guide foot 21 which can be pre-set at a particular depth. Furthermore, the ophthalmic instrument 20 is disposable and does not block the view of the ophthalmologist while he is making incisions in the cornea of a patient in either cutting direction as does the ophthalmic instrument 10 of the prior art.

Referring to FIG. 8 and FIG. 9, the incisions in the cornea must be precise in order to obtain the proper result. Every step which can be eliminated in preparing the ophthalmic instrument 20 for performing a radial keratotomy aids the ophthalmologist in performing this procedures. By using a pre-set, sterile, disposable ophthalmic instrument, an ophthalmologist is able to concentrate on performing the procedure.

From the foregoing, it can be seen that an ophthalmic instrument for performing radial keratotomy on the cornea of a patient has been described. It should be noted that the sketches are not drawn to scale and that distance of and between the figures are not to be considered significant.

Accordingly, it is intended that the foregoing disclosure and showing made in the drawing shall be considered only as an illustration of the principles of the present invention.

What is claimed is:

1. An ophthalmic instrument for use in performing radial keratotomy on the cornea of a patient for correcting myopia and/or astigmatism of the patient, the ophthalmic instrument comprising:

a surgical blade having a suitable width for making an incision into the cornea of the patient;

an elongated handle to which the surgical blade is fixedly coupled; and a depth-guide which is a hollow, cylindrical member slidably coupled to the elongated handle, the member having a pair of a protruding arms, each of which has a first end and a rounded second end and which extend parallel to each other and to the longitudinal axis of the hollow, cylindrical member from the first ends of the protruding arms for most of their length and then sharply converge adjacent, but not contiguous to the rounded second ends of the protruding arms, the second ends of the protruding arms being spaced apart a distance slightly greater than the width of the surgical blade whereby the rounded second ends of the protruding arms slidably rest on the surface of the cornea in order to control the incision depth of the surgical blade.

2. An ophthalmic instrument according to claim 1 for use in performing radial keratotomy on the cornea of a patient for correcting myopia and/or astigmatism of the patient, the ophthalmic instrument wherein the elongated handle is formed out of a plastic material and wherein the depth-guide is also formed out of a plastic material.

3. An ophthalmic instrument according to claim 2 wherein the depth-guide has its position on the elongated handle pre-set to a depth in the range of 0.20 millimeters to 1.2 millimeters and fixedly secured so that opthalmic surgeon does need to adjust the position of the depth-guide in order to obtain the correct depth of the incision.

* * * * *